United States Patent
Brockway et al.

(10) Patent No.: US 7,761,158 B2
(45) Date of Patent: Jul. 20, 2010

(54) DETECTION OF HEART FAILURE DECOMPENSATION BASED ON CUMULATIVE CHANGES IN SENSOR SIGNALS

(75) Inventors: Marina Brockway, Shoreview, MN (US); John Troiani, Maple Grove, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 1014 days.

(21) Appl. No.: 11/312,277

(22) Filed: Dec. 20, 2005

(65) Prior Publication Data

US 2007/0142732 A1 Jun. 21, 2007

(51) Int. Cl.
*A61N 1/18* (2006.01)
(52) U.S. Cl. ...................................................... 607/18
(58) Field of Classification Search ................. 600/373, 600/374, 377, 382, 508, 509, 513–515, 519, 600/547, 586; 607/4–9, 11, 14, 15, 17–20, 607/26, 28, 30, 32
See application file for complete search history.

(56) References Cited

U.S. PATENT DOCUMENTS

| | | | |
|---|---|---|---|
| 4,562,841 A | 1/1986 | Brockway et al. | |
| 4,953,551 A | 9/1990 | Mehra et al. | |
| 5,036,849 A | 8/1991 | Hauck et al. | |
| 5,133,353 A | 7/1992 | Hauser | |
| 5,170,784 A | 12/1992 | Ramon et al. | |
| 5,179,945 A | 1/1993 | Van Hofwegen et al. | |
| 5,203,348 A | 4/1993 | Dahl et al. | |
| 5,209,229 A | 5/1993 | Gilli | |
| 5,230,337 A | 7/1993 | Dahl et al. | |
| 5,261,400 A | 11/1993 | Bardy | |
| 5,284,136 A | 2/1994 | Hauck et al. | |
| 5,292,338 A | 3/1994 | Bardy | |
| 5,300,106 A | 4/1994 | Dahl et al. | |
| 5,301,677 A | 4/1994 | Hsung | |
| 5,313,953 A | 5/1994 | Yomtov et al. | |
| 5,314,430 A | 5/1994 | Bardy | |
| 5,314,459 A | 5/1994 | Swanson et al. | |

(Continued)

FOREIGN PATENT DOCUMENTS

WO   WO 92/20402   11/1992

(Continued)

OTHER PUBLICATIONS

Renee Hartz et al., *New Approach to Defibrillator Insertion*, J. Thoracic Cardiovascular Surgery, vol. 97, pp. 920-922, (1989).

(Continued)

*Primary Examiner*—Carl H Layno
*Assistant Examiner*—Frances P Oropeza
(74) *Attorney, Agent, or Firm*—Hollingsworth & Funk, LLC

(57) ABSTRACT

Systems, devices and methods provide for evaluation of heart failure symptoms. Sensor data associated with one or more symptoms of heart failure are acquired and trended. Statistical features, such as slope, are extracted from the data trend in a moving window and are used to develop a cumulative sum. The cumulative sum is compared to a threshold value or V-mask to detect a shift in cumulative sum indicating changes in heart failure symptoms. A shift beyond the threshold value may trigger an alert or implementation of therapy.

27 Claims, 11 Drawing Sheets

U.S. PATENT DOCUMENTS

| | | |
|---|---|---|
| 5,318,597 A | 6/1994 | Hauck et al. |
| 5,331,966 A | 7/1994 | Bennett et al. |
| 5,360,442 A | 11/1994 | Dahl et al. |
| 5,366,496 A | 11/1994 | Dahl et al. |
| 5,372,606 A | 12/1994 | Lang et al. |
| 5,376,106 A | 12/1994 | Stahmann et al. |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,411,539 A | 5/1995 | Neisz |
| 5,439,482 A | 8/1995 | Adams et al. |
| 5,441,518 A | 8/1995 | Adams et al. |
| 5,468,254 A | 11/1995 | Hahn et al. |
| 5,531,779 A | 7/1996 | Dahn et al. |
| 5,540,727 A | 7/1996 | Tockman et al. |
| 5,545,186 A | 8/1996 | Olson et al. |
| 5,545,202 A | 8/1996 | Dahl et al. |
| 5,603,732 A | 2/1997 | Dahl et al. |
| 5,620,466 A | 4/1997 | Haefner et al. |
| 5,634,938 A | 6/1997 | Swanson et al. |
| 5,641,326 A | 6/1997 | Adams |
| 5,662,688 A | 9/1997 | Haefner et al. |
| 5,697,953 A | 12/1997 | Kroll et al. |
| 5,704,365 A | 1/1998 | Albrecht et al. |
| 5,724,984 A | 3/1998 | Arnold et al. |
| 5,827,326 A | 10/1998 | Kroll et al. |
| 5,836,987 A | 11/1998 | Baumann et al. |
| 5,855,593 A | 1/1999 | Olson et al. |
| 5,895,414 A | 4/1999 | Sanchez-Zambrano |
| 5,916,243 A | 6/1999 | KenKnight et al. |
| 5,957,956 A | 9/1999 | Kroll et al. |
| 6,044,298 A | 3/2000 | Salo et al. |
| 6,055,454 A | 4/2000 | Heemels |
| 6,141,581 A | 10/2000 | Olson et al. |
| 6,148,230 A | 11/2000 | KenKnight |
| 6,259,947 B1 | 7/2001 | Olson et al. |
| 6,280,462 B1 | 8/2001 | Hauser et al. |
| 6,336,903 B1 | 1/2002 | Bardy |
| 6,358,203 B2 | 3/2002 | Bardy |
| 6,360,127 B1 | 3/2002 | Ding et al. |
| 6,368,284 B1 | 4/2002 | Bardy |
| 6,398,728 B1 | 6/2002 | Bardy |
| 6,409,675 B1 | 6/2002 | Turcott |
| 6,415,174 B1 | 7/2002 | Bebehani et al. |
| 6,438,410 B2 | 8/2002 | Hsu et al. |
| 6,440,066 B1 | 8/2002 | Bardy |
| 6,480,733 B1 | 11/2002 | Turcott |
| 6,487,443 B2 | 11/2002 | Olson et al. |
| 6,491,639 B1 | 12/2002 | Turcott |
| 6,512,940 B1 | 1/2003 | Brabec et al. |
| 6,522,915 B1 | 2/2003 | Ceballos et al. |
| 6,564,106 B2 | 5/2003 | Guck et al. |
| 6,597,951 B2 | 7/2003 | Kramer et al. |
| 6,607,509 B2 | 8/2003 | Bobroff et al. |
| 6,615,083 B2 | 9/2003 | Kupper |
| 6,622,046 B2 | 9/2003 | Fraley et al. |
| 6,645,153 B2 | 11/2003 | Kroll et al. |
| 7,308,309 B1 * | 12/2007 | Koh .............. 607/17 |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082658 A1 | 6/2002 | Heinrich et al. |
| 2002/0091414 A1 | 7/2002 | Bardy et al. |
| 2002/0095184 A1 | 7/2002 | Bardy et al. |
| 2002/0103510 A1 | 8/2002 | Bardy et al. |
| 2002/0107544 A1 | 8/2002 | Ostroff et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2003/0004546 A1 | 1/2003 | Casey |
| 2003/0004552 A1 | 1/2003 | Plombon et al. |
| 2003/0023175 A1 | 1/2003 | Arzbaecher et al. |
| 2003/0036778 A1 | 2/2003 | Ostroff et al. |
| 2003/0045904 A1 | 3/2003 | Bardy et al. |
| 2003/0069609 A1 | 4/2003 | Thompson |
| 2003/0088278 A1 | 5/2003 | Bardy et al. |
| 2003/0088279 A1 | 5/2003 | Rissmann et al. |
| 2003/0088280 A1 | 5/2003 | Ostroff |
| 2003/0088281 A1 | 5/2003 | Ostroff et al. |
| 2003/0088282 A1 | 5/2003 | Ostroff |
| 2003/0088283 A1 | 5/2003 | Ostroff |
| 2003/0088286 A1 | 5/2003 | Ostroff et al. |
| 2003/0097153 A1 | 5/2003 | Bardy et al. |
| 2003/0212436 A1 | 11/2003 | Brown |
| 2004/0215238 A1 | 10/2004 | van Dam et al. |
| 2004/0230230 A1 | 11/2004 | Lindstrom et al. |
| 2004/0230243 A1 | 11/2004 | Haefner et al. |

FOREIGN PATENT DOCUMENTS

| | | |
|---|---|---|
| WO | 2004/062484 | 7/2004 |

OTHER PUBLICATIONS

1993, Theofilos M. Kolettis, MD, PhD et al., *Submammary Implantation of a Cardioverter-Defibrillator with a Nonthoractomy Lead System*, Am. Heart J., vol. 126, pp. 1222-1223 (Nov. 1993).

1971, John C. Schuder et al., *Transthoracic Ventricular Defibrillation in the Dog with Truncated and Untruncated Exponential Stimuli*, IEEE Trans. On Bio-Medical Engin., vol. BME-18, No. 6, pp. 410-415 (Nov. 1971).

1974, John C. Schuder et al., *Ventricular Defibrillation in the Dog Using Implanted and Partially Implanted Electrode Systems*, Am. J. of Cardiology, vol. 33, pp. 243-247 (Feb. 1974).

1970, John C. Schuder et al., *Experimental Ventricular Defibrillation with an Automatic and Completely Implanted System*, Trans. Am. Soc. Artif. Int. Organs, vol. 16, pp. 207-212 (1970).

2001, Karel Smits & Marek Malik, *Defibrillation Threshold (DFT) Model of a Fully Subcutaneous ICD System*, Europace Supplements, vol. 2, Jun. 2001 at B83.

1986, Stirbis et al., *Optmizing the Shape of Implanted Artificial Pacemakers*, Kaunas Medical Institute. Translated from Meditsinskaya Tekhnika, No. 6, pp. 25-27 (1986).

2001, Charles T. Leng et al., *Lead Configuration for Defibrillator Implantation in a Patient with Congenital Heart Disease and a Mechanical Prosthetic Tricuspid Valve*, PACE, vol. 24, No. 8, pp. 1291-1292 (Aug. 2001).

1999, Park & Pollock, *Use of an Implantable Cardioverter Defibrillator in an Eight-Month-Old Infant with Ventricular Fibrillation Arising from a Myocardial Fibroma*, PACE, vol. 22, No. 1, pp. 138-139 (Jan. 1999).

2001, Rainer Gradaus M.D. et al., *Nonthoracotomy Implantable Cardioverter Defibrillator Placement in Children: Use of a Subcutaneous Array Leads and Abdominally Placed Implantable Cardioverter Defibrillators in Children*, J. of Cardiovascular Electrophysiology, vol. 12, No. 3, pp. 356-360 (Mar. 2001).

* cited by examiner

DETECTION OF HEART FAILURE DECOMPENSATION BASED ON CUMULATIVE CHANGES IN SENSOR SIGNALS

FIELD OF THE INVENTION

The present invention relates generally to evaluation of heart failure symptoms.

BACKGROUND OF THE INVENTION

Heart failure is an abnormality of cardiac function that causes cardiac output to fall below a level adequate to meet the metabolic demand of peripheral tissues. Heart failure is usually referred to as congestive heart failure (CHF) due to the accompanying venous and pulmonary congestion. Congestive heart failure may have a variety of underlying causes, including ischemic heart disease (coronary artery disease), hypertension (high blood pressure), and diabetes, among others.

Because of the need for early evaluation heart failure symptoms, an effective approach to monitoring and early diagnosis is desired. Evaluating physiological sensor information may allow early intervention, preventing serious heart failure decompensation and hospitalization. The present invention provides early evaluation of disease symptoms and opportunities for effective treatment and offers various advantages over the prior art.

SUMMARY OF THE INVENTION

The present invention is directed to methods and devices for evaluation of heart failure symptoms. One embodiment of the invention is directed to a method for evaluating heart failure symptoms. Sensor data associated with one or more symptoms of heart failure are acquired. A cumulative sum is developed using the sensor data. One or more heart failure symptoms are evaluated based on the cumulative sum. In some embodiments, the sensor data is acquired within a moving time window.

The acquired sensor data may be associated with one or more respiration parameters and/or one or more cardiac parameters, or other parameters associated with heart failure symptoms. In one configuration, acquiring the sensor data involves generating a transthoracic impedance signal and extracting statistical features from the transthoracic impedance signal.

The sensor data may be acquired from a single sensor or from multiple sensors. If multiple sensors are used, the cumulative sum may be developed through calculation of a multivariate cumulative sum.

The cumulative sum can be developed based on the slope of trended sensor data. The cumulative sum is compared to a threshold or V-mask to detect shifts in the sensor data indicating changes in CHF symptoms. In some configurations, an alert is generated based on the shift. In other configurations, a shift in the cumulative sum triggers implementation or modification of therapy, such as cardiac pacing therapy, drug therapy, or other type of therapy used to treat heart failure.

Another embodiment of the invention involves a medical device used for evaluating CHF symptoms. The medical device includes sensing circuitry configured to acquire sensor data associated with one or more symptoms of heart failure. A diagnostics processor coupled to the sensing circuitry is configured to develop a cumulative sum using the sensor data. The diagnostics processor evaluates the heart failure symptoms based on the cumulative sum. In some embodiments, at least one of the sensing circuitry and the diagnostics processor comprises an implantable component.

The diagnostics processor is configured to extract statistical features from the sensor data and use the extracted features to develop the cumulative sum. According to a more specific application, the diagnostics processor may trend the sensor data, determine a slope of the trend, and develop the cumulative sum using the slope.

In one configuration, the sensing circuitry includes a sensor configured to sense transthoracic impedance and to acquire sensor data based on the transthoracic impedance signal.

The medical device of claim may further include an alarm unit coupled to the diagnostics processor. If the diagnostics processor detects a shift in the cumulative sum exceeding a specified threshold, the diagnostics processor may send a control signal to the alarm unit to issue an alert.

In another configuration, the medical device may also include a therapy control unit coupled to the diagnostics processor. The therapy control unit is used to control a therapy, such as a cardiac pacing therapy, based on the evaluation of the one or more heart failure symptoms.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
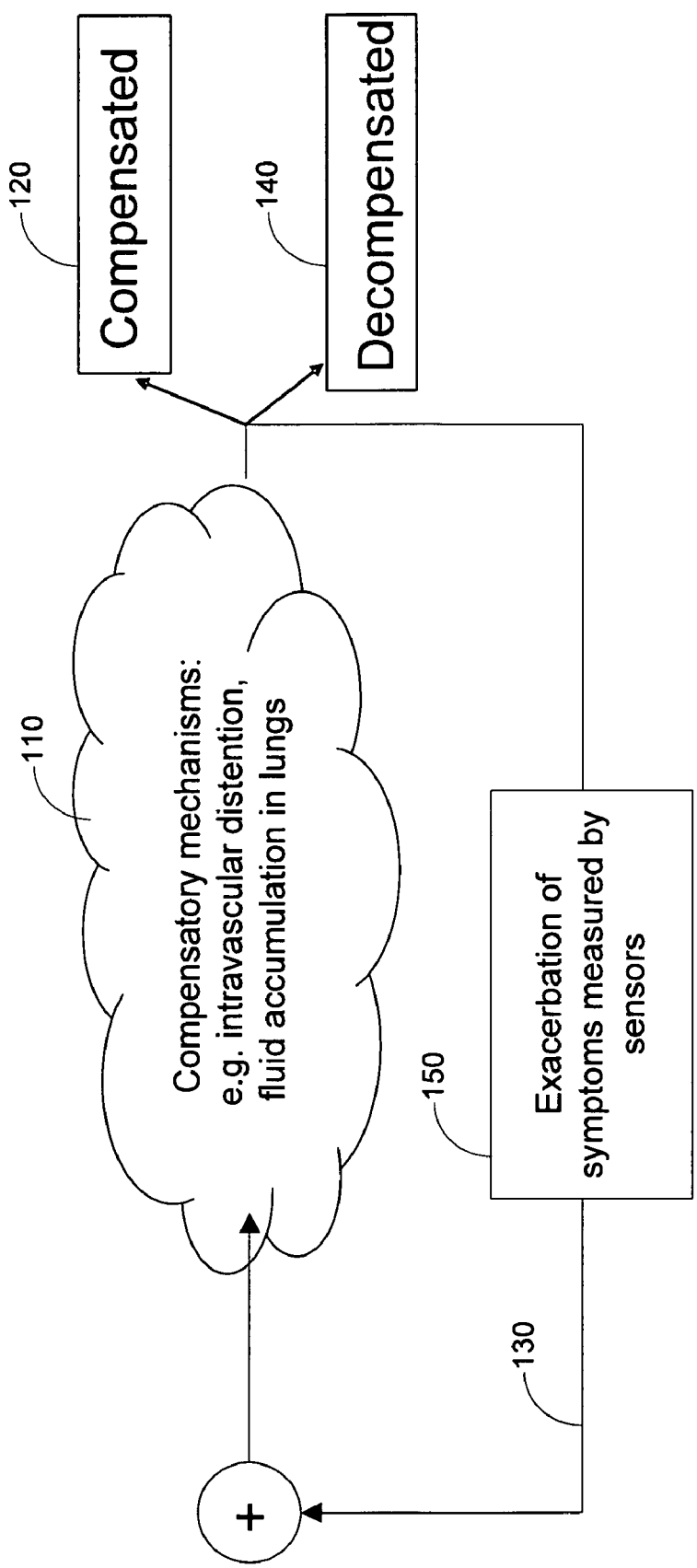
FIG. 1 is a diagram illustrating the typical physiological response to progression of congestive heart failure.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

The present invention is directed to detecting early onset of heart failure decompensation based on analysis of sensor data. The sensor data analysis involves detecting cumulative changes in sensed signals associated with heart failure symptoms. The systems and methods described herein are particularly applicable to disease symptoms that tend to accumulate during compensatory system overload.

FIG. 1 is a diagram illustrating the typical physiological response to progression of CHF. CHF triggers a number of compensatory mechanisms 110 evidenced in increased heart rate, increased cardiac muscle mass, activation of Renin-Angiotensin-Aldosterone System and vasoconstriction. During a first phase, the patient's CHF is compensated 120 when physiological systems are able to counteract the heart's reduced pumping efficiency to a certain extent. The initially palliative, compensatory mechanisms may serve to mask the patient's underlying condition. As CHF progresses, a positive feedback loop 130 results as the patient's body attempts to compensate for the heart's decreased pumping efficiency, sometimes producing a rapid accumulation of symptoms. Unchecked, CHF eventually transitions to the decompensated state 140 when physiological systems are no longer able to compensate for the cardiac loss of power. Systems and methods in accordance with embodiments of the present invention provide for monitoring 150 sensor data to detect the exacerbation of symptoms associated with CHF decompensation like fluid accumulation in the lungs, respiratory distress, disordered breathing, peripheral edema, and/or other symptoms.

Figure 2:
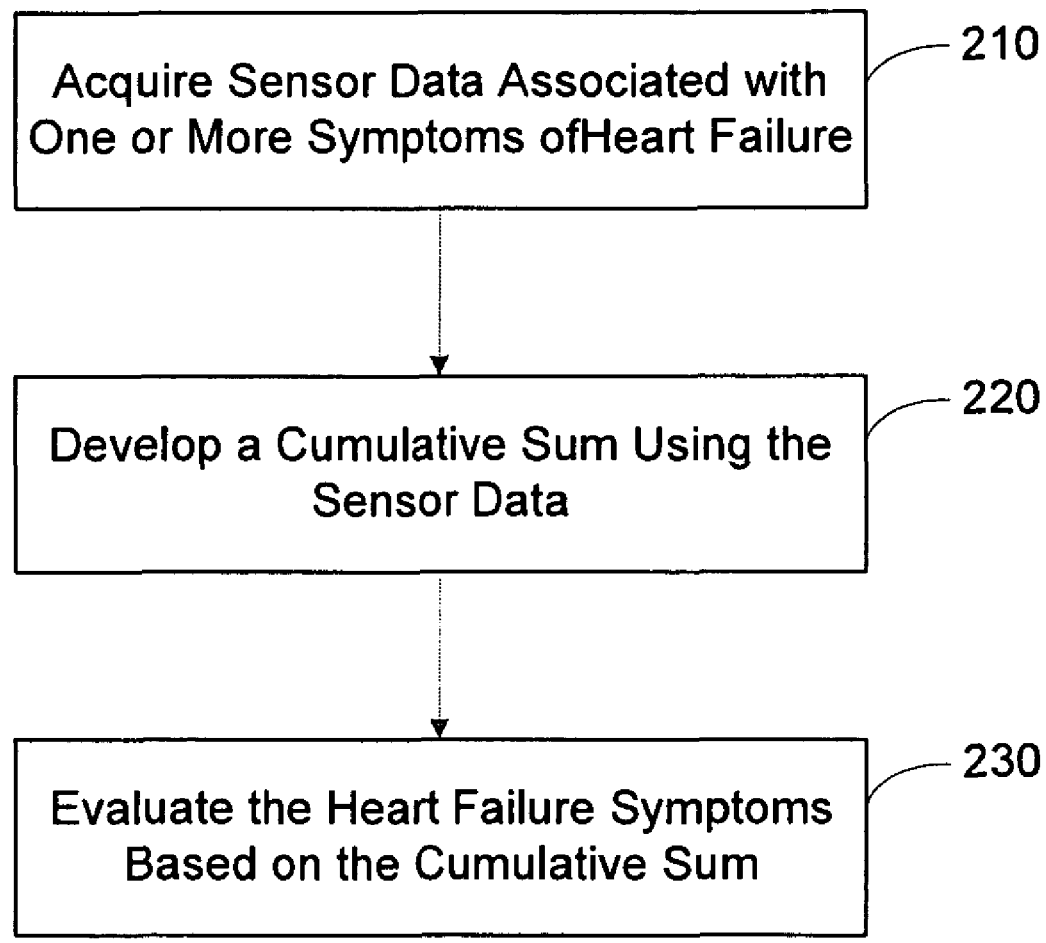
FIG. 2 is a flowchart illustrating a method for evaluating heart failure symptoms in accordance with embodiments of the invention.

FIG. 2 is a flowchart illustrating a method for evaluating CHF symptoms in accordance with embodiments of the invention. Sensor data associated with one or more symptoms of heart failure are acquired 210. The sensor data may be acquired using implantable sensors, patient-external sensors, partially implantable sensors and/or patient response systems which generate signals associated with various CHF symptoms. A cumulative sum is developed 220 using the sensor data. The heart failure symptoms are evaluated 230 based on the cumulative sum.

In one implementation, acquiring the sensor data involves acquiring discrete sample values of a filtered sensor signal. The development of the cumulative sum involves determining the cumulative sum from the discrete sample values. In another implementation, acquiring the sensor data involves extracting statistical features from sensor signals. For example, the sensor data may be trended and slopes of the trend extracted at a series of data points within a moving window. The slopes determined from the trended data may be used to develop the cumulative sum. Alternatively, the cumulative sum may be based on other statistical or morphological features of the data trend.

The cumulative sum can be used to evaluate one or more of the patient's CHF symptoms, to diagnose or detect a presence of CHF and/or to track the progression or regression of CHF or various symptoms associated with CHF. Based on the evaluation, one or more clinical actions may be taken, such as implementation of a therapy or generation of an alarm.

Figure 3:
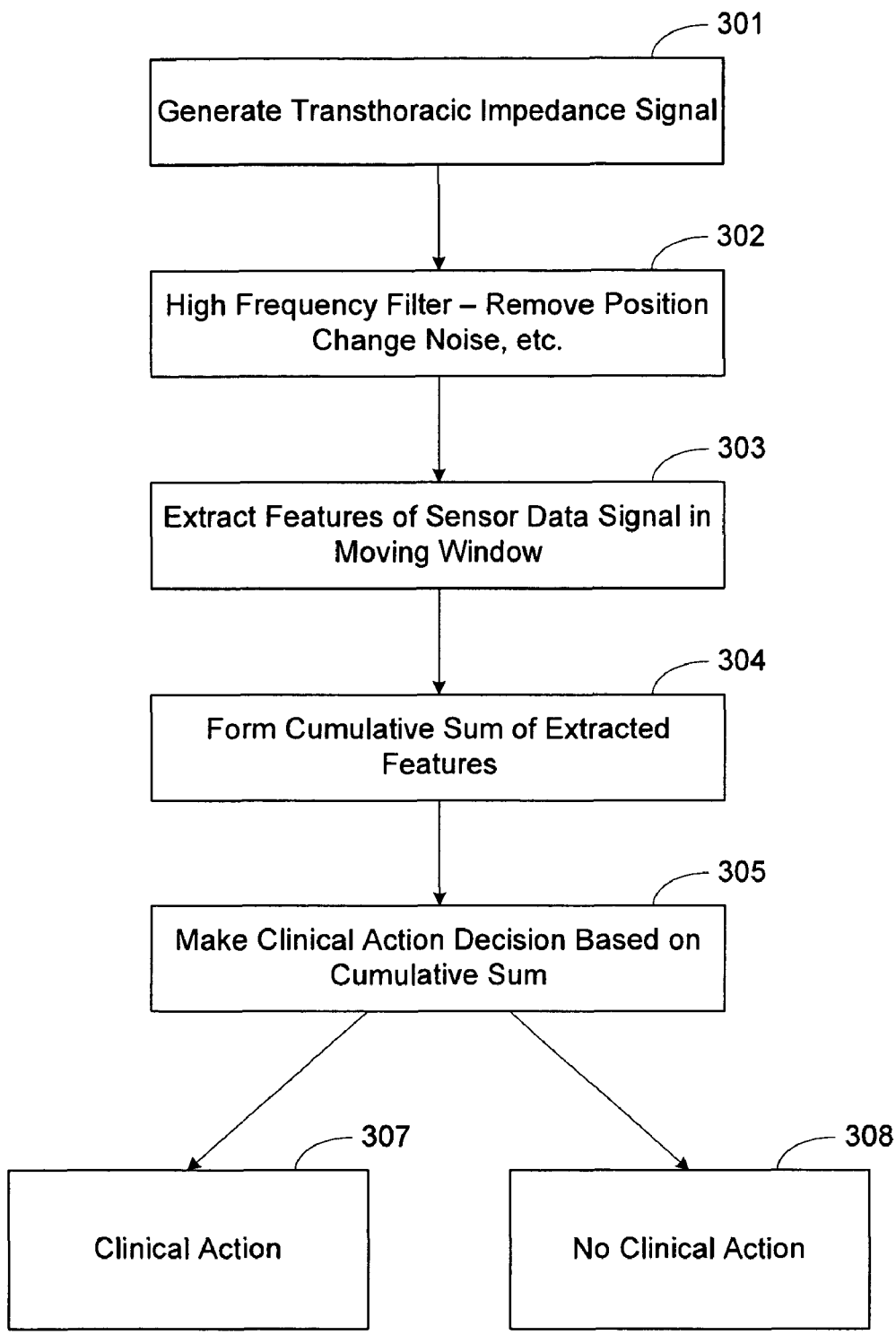
FIG. 3 is a flowchart illustrating initiation of clinical action based on persistent shifts in data associated with heart failure symptoms in accordance with further embodiments of the invention.

Initiation of clinical action based on evaluation of heart failure symptoms is illustrated in FIG. 3. As an example, the process involves monitoring for increased fluid buildup in the lungs, a symptom of heart failure which often leads to hospitalization. Fluid in the lungs can be detected via implantable transthoracic impedance measurements. Electrodes used for implantable transthoracic impedance measurement may be positioned on the patient's chest, or may be implanted within the chest. In one implementation, the electrodes used for the impedance measurement are electrodes used in conjunction with an implantable cardiac device such as a pacemaker or defibrillator.

A signal corresponding to the patient's transthoracic impedance is generated 301 at the impedance sense electrodes and filtered 302. The sensor signal is processed to extract key characteristics 303 of the signal in a moving window. A cumulative sum of the extracted features is performed 304. In one embodiment, the slope of a linear fit of the trended sensor data for a moving window is extracted, such as about a 14 day moving window, although other lengths for the moving window may be used. Statistical or morphological features of the data signal other than the slope may alternatively be extracted and used to form the cumulative sum. The length of the moving window may be adjusted to allow averaging over a longer window to reduce the possibility of detection of false trends.

The cumulative sum is evaluated to detect persistent shifts in the trended signal data or extracted signal features which would indicate changes in lung fluid. In some embodiments, evaluation to detect changes in the patient's symptoms indicated by shifts in the sensor data involves comparing the cumulative sum to one or more thresholds. A clinical action decision is made 305 based on the shifts indicated by the cumulative sum. For example, if the cumulative sum indicates that the severity of the patient's lung fluid is sufficiently low and stable, no clinical action is taken 308. If the cumulative sum indicates a persistent and sufficiently large shift in the amount of lung fluid, clinical action, such as generating an alert and/or initiating, modifying or terminating delivery of therapy, may be taken 307.

The threshold and/or the length of the moving window may be selected based on patient characteristics. For example, clinical characteristics such as etiology and activity tolerance (e.g., based on NYHA classification), and/or demographic characteristics such as age may be used to segment the population to adjust the threshold and/or moving window. Additionally or alternatively, physicians may set or adjust the threshold and/or moving window length.

Figure 4A:
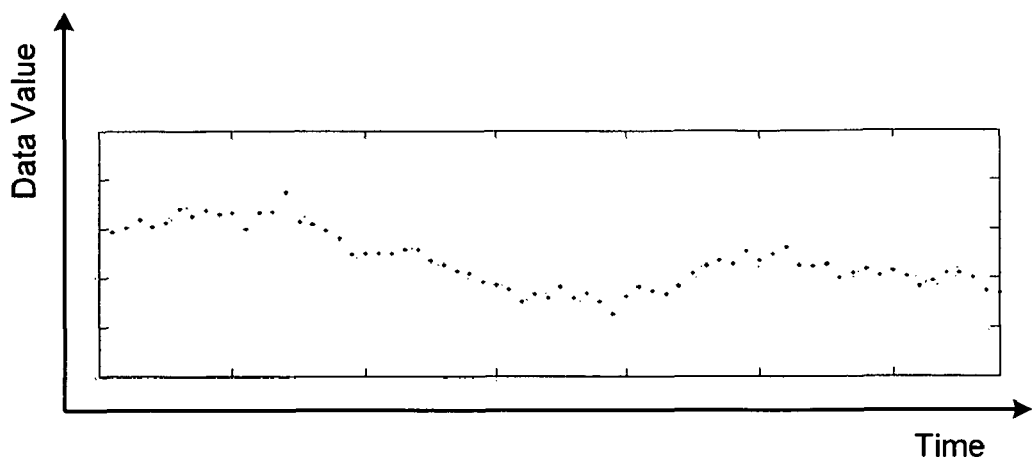
FIGS. 4A-4F provide graphs illustrating heart failure symptom evaluation based on cumulative changes in sensor data for three rates of decompensation in accordance with embodiments of the invention.
Figure 4B:
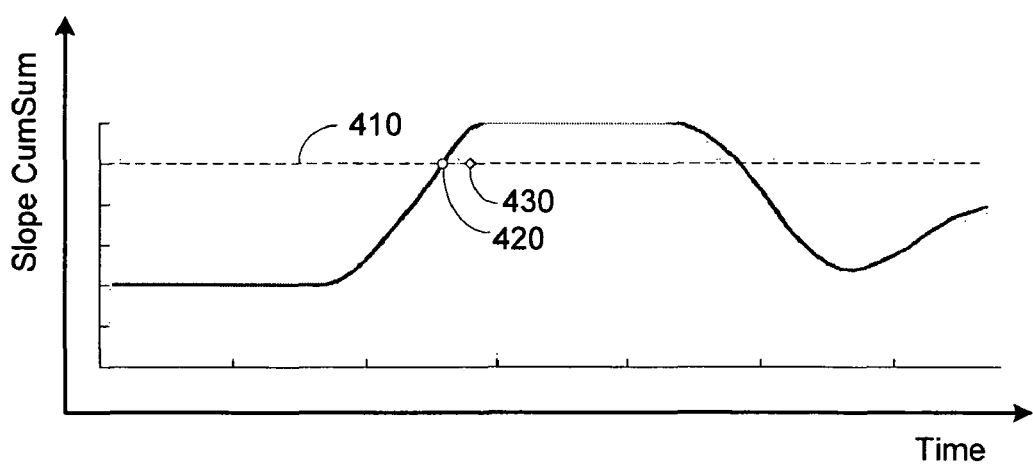
Figure 4C:
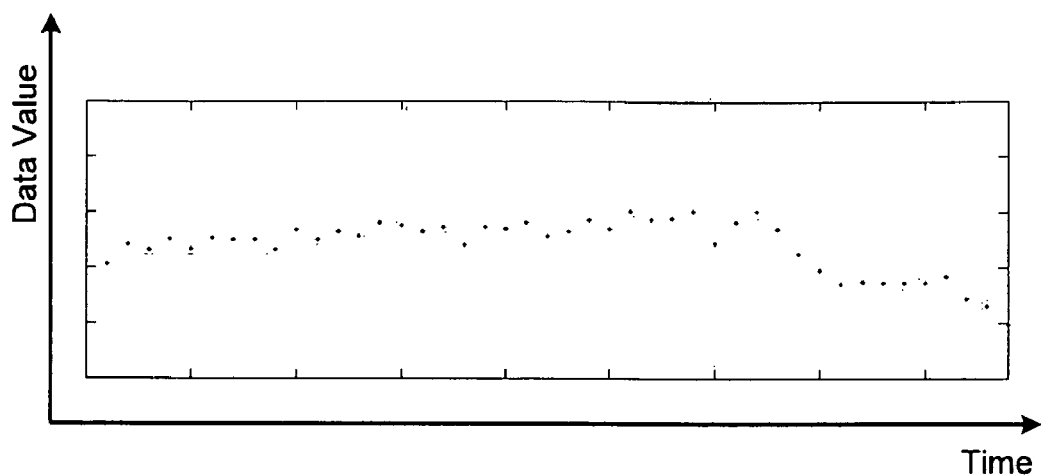
Figure 4D:
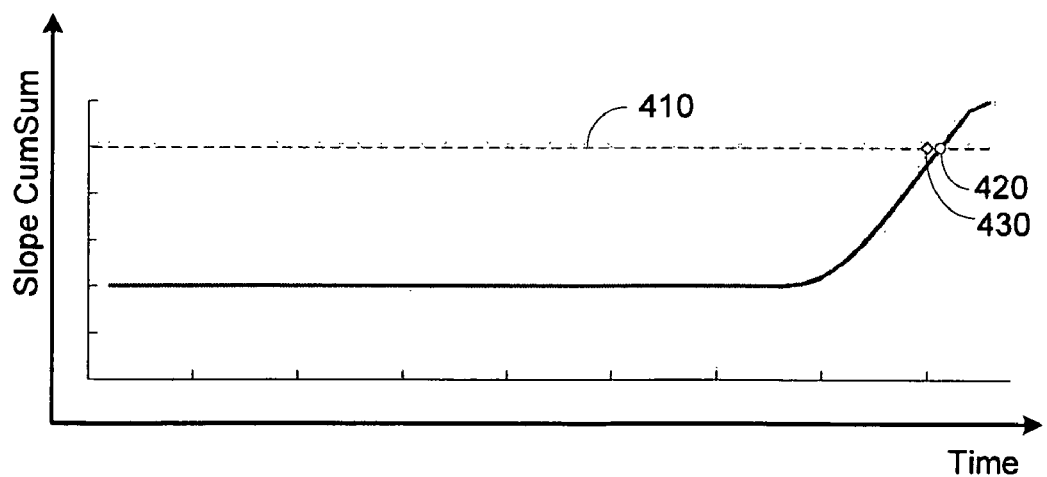
Figure 4E:
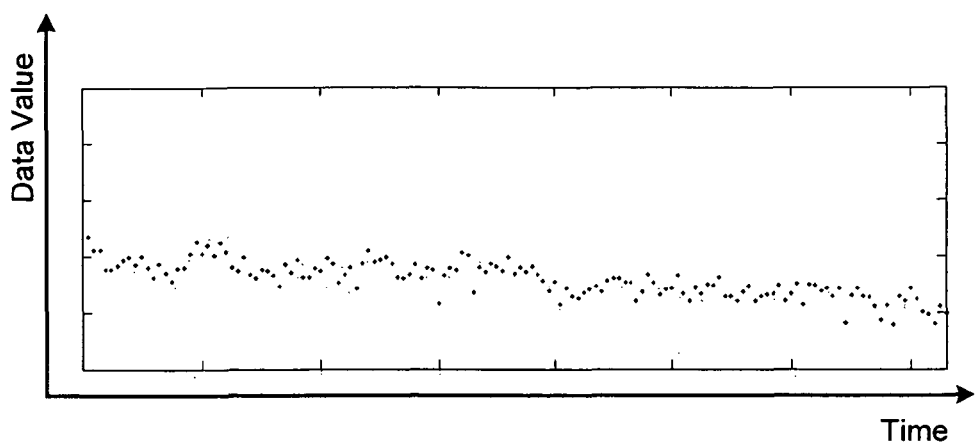
Figure 4F:
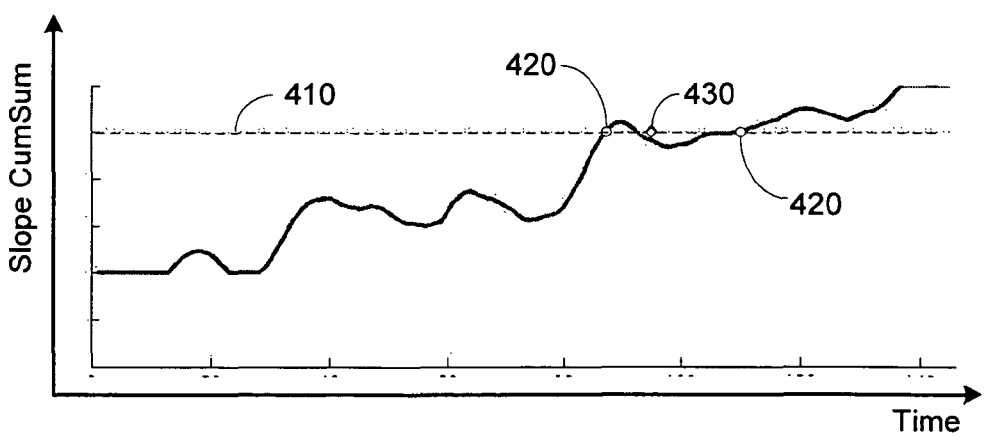

FIGS. 4A-4F provide graphs illustrating heart failure symptom evaluation based on cumulative changes in sensor data for three rates of decompensation in accordance with embodiments of the invention. FIGS. 4A and 4B are graphs of filtered sensor data and the cumulative sum of the extracted slope of the filtered sensor data, respectively, for decompensation at a medium rate. FIGS. 4C and 4D illustrate rapid decompensation and FIGS. 4E and 4F illustrate slow decompensation.

In each of these cases, the cumulative sum of the slope of the trended data (slope cumsum) is evaluated in a moving window. The slope cumsum is compared to a threshold value 410. In one implementation, an alert or other clinical action may be taken at the point 420 when the slope cumsum exceeds the threshold value as indicated in FIGS. 4B, 4D, and 4F. In another implementation, a V-mask may be used to determine if clinical action should be taken. The V-mask involves evaluation of both the slope of the shift and a decision interval. FIGS. 4B, 4D, and 4F indicate the point 430 at which the clinical action decision is made if a V-mask is used.

Figure 5A:
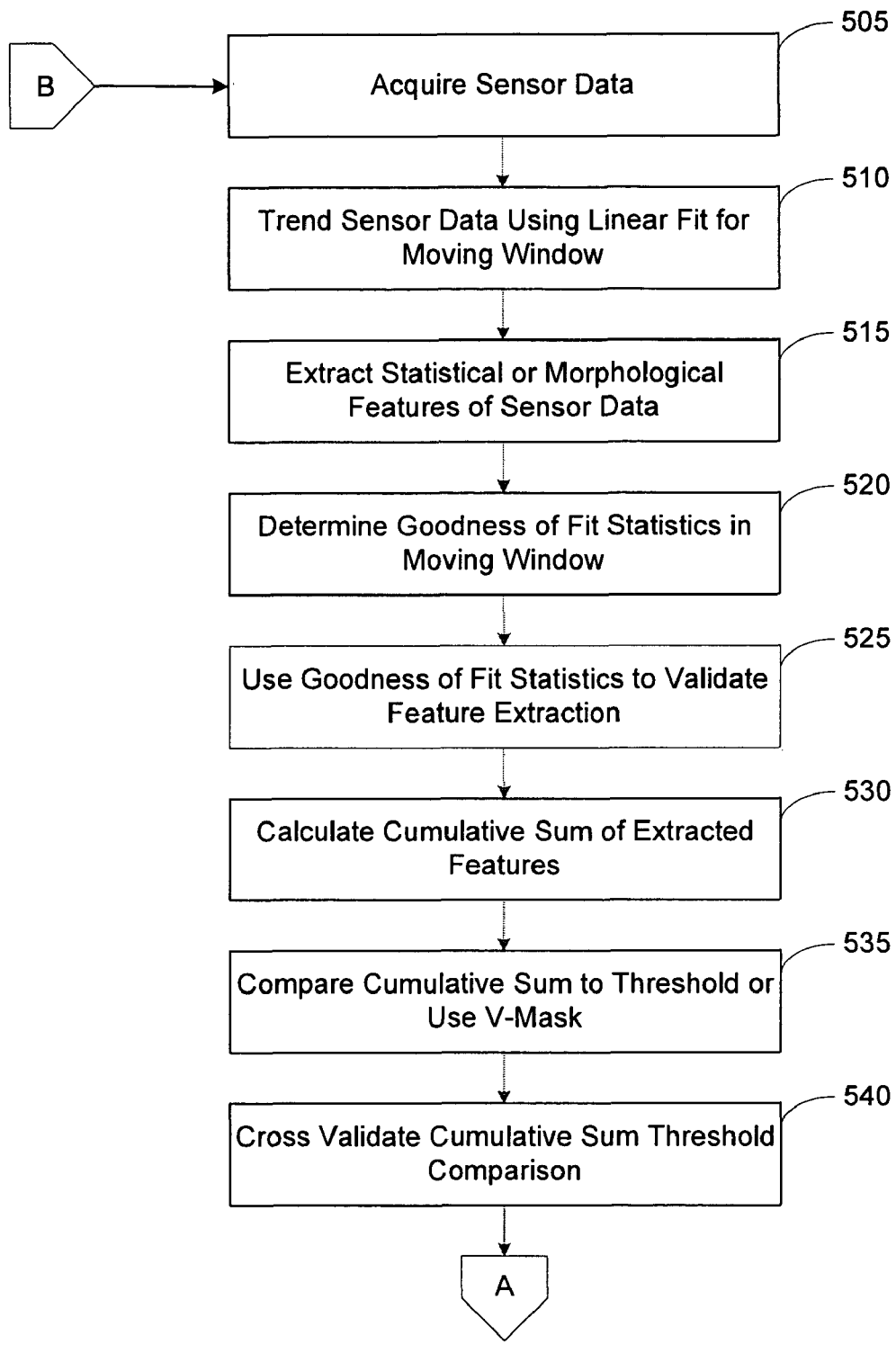
FIGS. 5A and 5B illustrate a flowchart of a method for evaluation of heart failure symptoms in accordance with another embodiment of the invention.
Figure 5B:
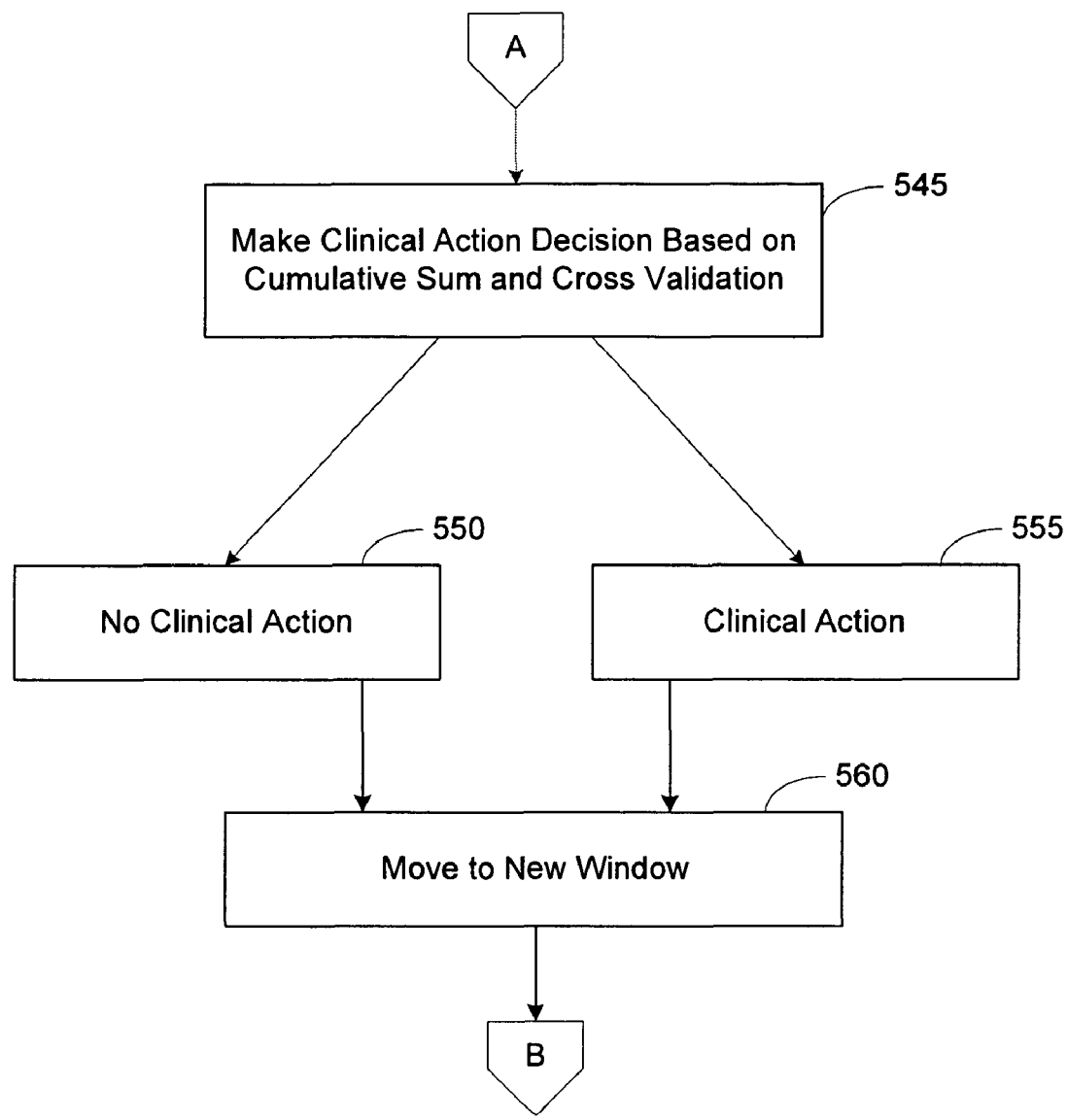

Shown in FIGS. 5A and 5B is a flowchart of a method for evaluation of heart failure symptoms in accordance with another embodiment. A representative set of parameters which may be used to evaluate heart failure symptoms using methodologies of the present invention include implantable transthoracic impedance, respiratory rate, tidal volume, forced expiratory volume, S3 or S4 gallop heart sounds, heart rate variability, weight, activity, and apnea hypopnea index, among other parameters indicative of CHF symptoms.

Sensor data is acquired 505 and filtered by averaging to remove short-term noises, e.g., due to posture changes. The sensor data is trended 510 using a linear fit of the data in a moving window. Morphological or statistical features of the sensor data are extracted 515. As previously described, one example of feature extraction involves determining the slope of the data trend. Another option for feature extraction is determining the time series skewness, which may be calculated using Equation 1.

$$\text{skewness} = \frac{\sum_{i=1}^{N}(Y_i - \overline{Y})^3}{(N-1)s^3} \quad [1]$$

where N is the number of data values, $Y_i$ is the $i^{th}$ data value, $\overline{Y}$ is the mean of the data values, and s is the standard deviation.

Optionally, goodness of fit statistics may also be collected 520 for the moving window and used 525 to validate the feature extraction.

Weighted and bounded cumulative sum statistics are calculated 530 for the extracted features. Persistent shifts in the data are identified using the cumulative sum statistics. This technique reflects the cumulative nature of the CHF compensatory mechanisms. The weights and bounds used for the cumulative sum calculation may be adjusted to enhance algorithm robustness with respect to short-term drifts, and to increase the specificity and/or sensitivity of CHF symptom analysis.

The cumulative sum is compared 535 to a threshold or V-mask. Optionally, the shift detection indicated by the threshold or V-mask comparison is validated 540 by testing the previously computed goodness of fit margins. For example, cross-validation of the shift detection may be performed by detecting an increase in the sum or squared errors (SSE). In some implementations, validation of the shift detection may be achieved based on corroborating parameters, such as through the acquisition and analysis of sensor data from multiple sensors.

A clinical action decision is made 545 (FIG. 5B) based on the comparison operation. If a shift is detected, clinical action is taken 555, which may involve generating an audible, visual, or vibratory alert to warn the patient and/or physician of the deterioration in the patient's condition. In some implementations, the alert may comprise an email, pager and/or telephone message. In some embodiments, the clinical action taken may involve implementing a therapy delivered to the patient, where implementation of the therapy may include initiating, terminating or modifying therapy. The therapy may comprise a pacing therapy delivered by an implantable pacemaker. Implementation of the pacing therapy may involve the use of pacing parameters selected to treat CHF symptoms. For example, the therapy may involve a cardiac resynchronization therapy and/or may include bi-ventricular pacing.

If a shift is not detected, no clinical action 550 is taken. The process continues 560 with the acquisition of data in a new moving window.

The process described in connection with FIGS. 5A and 5B may be enhanced by fusing additional sensor data associated with other ambulatory parameters and/or by performing regression adjustment in a multivariate cumulative sum calculation. Multisensor fusion may be implemented as a time lag combination between alerts issued on particular signals. The time lag may be suggested based on clinical or demographic patient characteristics and/or physician input.

Certain configurations of medical devices used to implement the CHF evaluation processes of the present invention are generally described as capable of various functions traditionally performed by an implantable cardioverter/defibrillator (ICD), and may operate in numerous cardioversion/defibrillation modes as are known in the art. Examples of ICD circuitry, structures and functionality, aspects of which may be incorporated in a medical device of the present invention, are disclosed in commonly owned U.S. Pat. Nos. 5,133,353; 5,179,945; 5,314,459; 5,318,597; 5,620,466; and 5,662,688, which are hereby incorporated herein by reference.

In particular configurations, systems and methods may perform functions traditionally performed by pacemakers, such as providing various pacing therapies as are known in the art, in addition to cardioversion/defibrillation therapies. Examples of pacemaker circuitry, structures and functionality, aspects of which may be incorporated in a medical device of the present invention, are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference. It is understood that medical device configurations may provide for non-physiologic pacing support in addition to, or to the exclusion of, bradycardia and/or anti-tachycardia pacing therapies.

A medical device in accordance with the present invention may implement diagnostic and/or monitoring functions as well as provide cardiac stimulation therapy. Examples of cardiac monitoring circuitry, structures and functionality, aspects of which may be incorporated in a medical device of the present invention, are disclosed in commonly owned U.S. Pat. Nos. 5,313,953; 5,388,578; and 5,411,031, which are hereby incorporated herein by reference.

Figure 6:
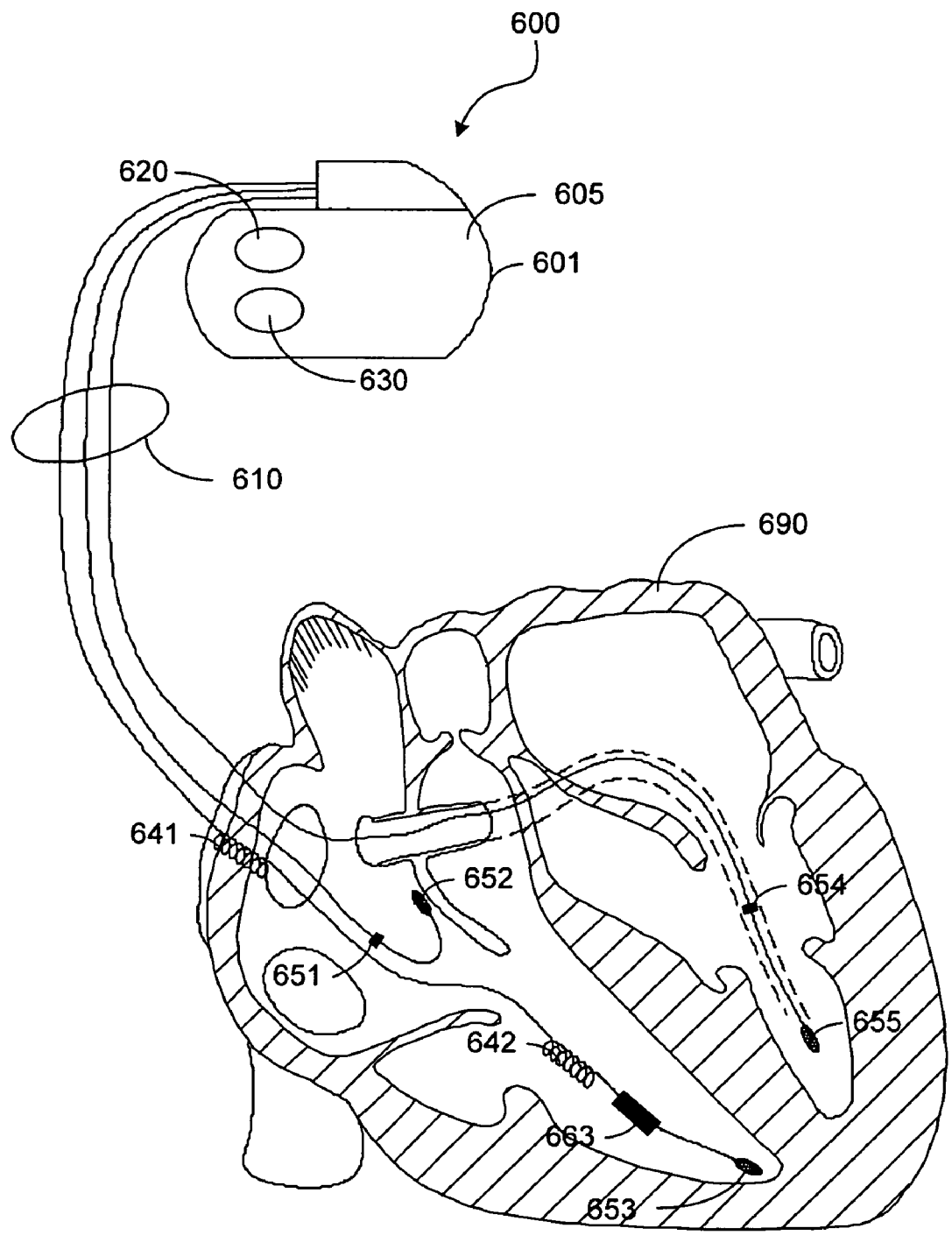
FIG. 6 illustrates an implantable medical device that may be used to evaluate heart failure symptoms in accordance with embodiments of the present invention.

Referring now to FIG. 6 there is illustrated an embodiment of a medical device configured to evaluate CHF symptoms and initiate appropriate clinical actions in accordance with embodiments of the present invention. In this illustrative example, the medical device comprises a cardiac rhythm management (CRM) device 600 including an implantable pulse generator 605 electrically and physically coupled to a lead system 610.

Portions of the lead system 610 are inserted into the patient's heart 690. The lead system 610 includes one or more electrodes and/or sensors configured to sense electrical cardiac activity of the heart, deliver electrical stimulation to the heart, sense transthoracic impedance, sense blood (internal filling) pressure, flow, and/or temperature, sense acceleration and/or body acoustics, and/or sense other physiological parameters of interest. Portions of the housing 601 of the pulse generator 605 may optionally serve as a can electrode.

Communications circuitry is disposed within the housing 601 for facilitating communication between the pulse generator 605 and an external communication device, such as a portable or bed-side communication station, patient-carried/ worn communication station (e.g., communicator), external programmer or advanced patient management system interface, for example. The communications circuitry may also facilitate unidirectional or bidirectional communication with one or more implanted, external, cutaneous, or subcutaneous physiologic or non-physiologic sensors, patient-input devices and/or information systems. In some embodiments, the communications circuitry may facilitate acquisition of externally acquired data, such as weight, which may be determined through an automated process or may be manually input by the patient via a device programmer wirelessly coupled to the CRM device 600.

The pulse generator 605 may optionally incorporate a motion sensor 620 that may be used to sense patient activity as well as various respiration and cardiac related conditions. For example, the motion sensor 620 may be optionally configured to sense sleep disordered breathing, activity level, and/or chest wall movements associated with respiratory effort, for example. The motion sensor 620 may be implemented as an accelerometer positioned in or on the housing 601 of the pulse generator 605. For a motion sensor implemented as an accelerometer, the motion sensor 620 may also provide respiratory, e.g. rales, coughing, and cardiac, e.g. S1-S4 heart sounds, murmurs, and other acoustic information. An accelerometer may be used to sense patient activity which may be used to determine CHF progression.

The lead system 610 and pulse generator 605 of the CRM 600 may incorporate one or more transthoracic impedance sensors that may be used to acquire the patient's respiration waveform, and/or other respiration-related information and/or acquire implantable impedance data associated with lung fluid accumulation. The transthoracic impedance sensor may include, for example, one or more electrodes 641, 642, 651-655, 663 positioned in relation to one or more chambers of the heart 690. The electrodes 641, 642, 651-655, 663 may be coupled to impedance drive/sense circuitry 630 positioned within the housing of the pulse generator 605.

In one implementation, impedance drive/sense circuitry 630 generates a current that flows through the tissue between an impedance drive electrode 651 and a can electrode on the housing 601 of the pulse generator 605. The voltage at an impedance sense electrode 652 relative to the can electrode changes as the patient's transthoracic impedance changes. The voltage signal developed between the impedance sense electrode 652 and the can electrode is detected by the impedance sense circuitry 630. Other locations and/or combinations of impedance sense and drive electrodes are also possible. Other sensors may additionally be coupled to the CRM 600.

The lead system 610 may include one or more cardiac pace/sense electrodes 651-655 positioned in, on, or about one or more heart chambers for sensing electrical signals from the patient's heart 690 and/or delivering pacing pulses to the heart 690. The sense/pace electrodes 651-655, such as those illustrated in FIG. 6, may be used to sense and/or pace one or more chambers of the heart, including the left ventricle, the right ventricle, the left atrium and/or the right atrium. The lead system 610 may include one or more defibrillation electrodes 641, 642 for delivering defibrillation/cardioversion shocks to the heart.

The lead system 610 may include one or more leads each having one or more electrodes that extend into the heart. FIG. 6 shows three such leads, one that extends into the right atrium, one that extends into the right ventricle, and one that extends into a coronary vein for placement at the surface of the left ventricle. The left ventricular lead, in particular, includes an LV distal electrode 655 and an LV proximal electrode 654 located at appropriate locations in or about the left ventricle for pacing and/or sensing the left ventricle. The left ventricular lead may be guided into the right atrium of the heart via the superior vena cava. From the right atrium, the left ventricular lead may be deployed into the coronary sinus ostium, the opening of the coronary sinus. The lead may be guided through the coronary sinus to a coronary vein of the left ventricle. This vein is used as an access pathway for leads to reach the surfaces of the left ventricle that are not directly accessible from the right side of the heart.

The pulse generator 605 may include circuitry for detecting cardiac arrhythmias and/or for controlling pacing or defibrillation therapy in the form of electrical stimulation pulses or shocks delivered to the heart through the lead system 610. The pulse generator 605 may also incorporate circuitry, structures and functionality of the implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243; 6,360,127; 6,597,951; and 6,993,389, which are hereby incorporated herein by reference.

For purposes of illustration, and not of limitation, various embodiments of devices implemented in accordance with the present invention are described herein in the context of medical devices that may be implanted under the skin in the chest region of a patient. A medical device may, for example, be implanted subcutaneously such that all or selected elements of the device are positioned on the patient's front, back, side, or other body locations suitable for sensing cardiac activity and/or delivering cardiac stimulation therapy. It is understood that elements of the medical device may be located at several different body locations, such as in the chest, abdominal, or subclavian region with electrode elements respectively positioned at different regions near, around, in, or on the heart.

The primary housing (e.g., the active or non-active can) of the medical device, for example, may be configured for positioning outside of the rib cage at an intercostal or subcostal location, within the abdomen, or in the upper chest region (e.g., subclavian location, such as above the third rib). In one implementation, one or more leads incorporating electrodes may be located in direct contact with the heart, great vessel or coronary vasculature, such as via one or more leads implanted by use of conventional transvenous delivery approaches. In another implementation, one or more electrodes may be located on the primary housing and/or at other locations about, but not in direct contact with the heart, great vessel or coronary vasculature.

In a further implementation, for example, one or more electrode subsystems or electrode arrays may be used to sense cardiac activity and deliver cardiac stimulation energy in a medical device configuration employing an active can or a configuration employing a non-active can. Electrodes may be situated at anterior and/or posterior locations relative to the heart. Examples of useful electrode locations and features that may be incorporated in various embodiments of the present invention are described in commonly owned, co-pending U.S. Publication No. 2004/0230230 and U.S. Pat. No. 7,499,750, which are hereby incorporated herein by reference.

Figure 7:
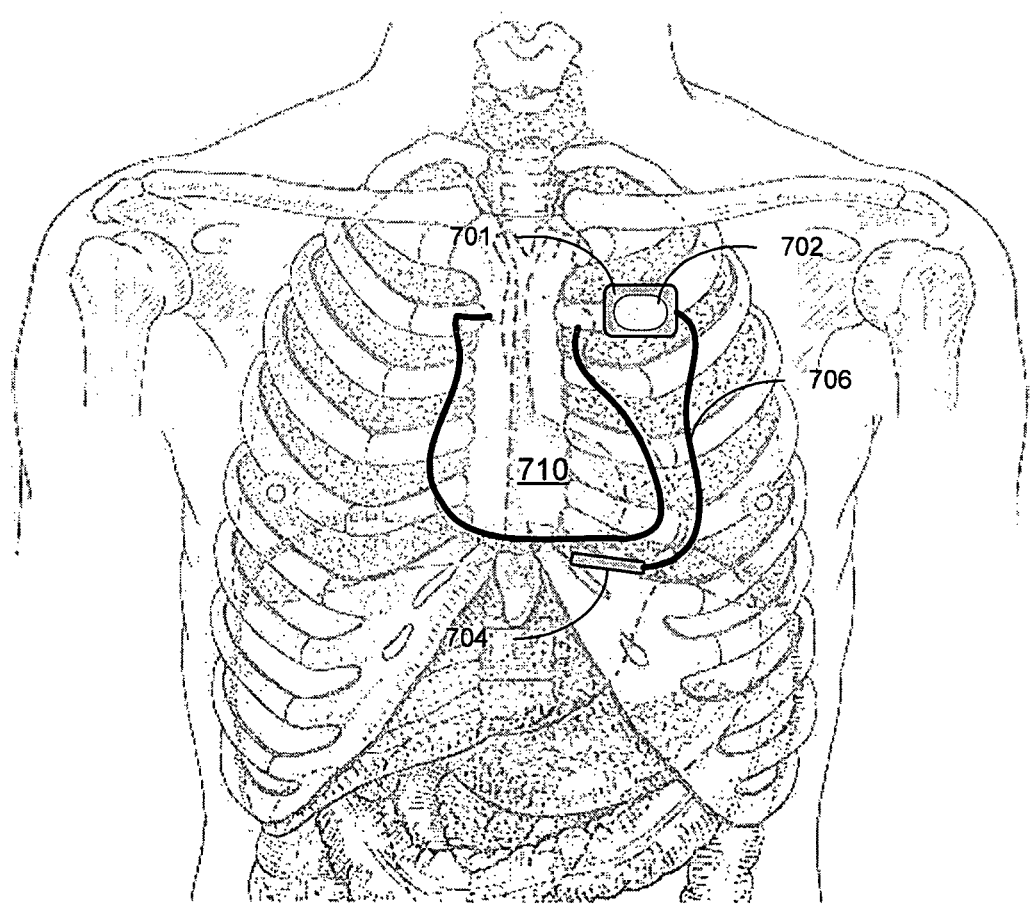
FIG. 7 is an illustration of an implantable medical device including a subcutaneous, non-intrathoracic lead assembly shown implanted outside the ribcage, the implantable medical device implemented to evaluate heart failure symptoms in accordance with embodiments of the invention.

In one configuration, as is illustrated in FIG. 7, electrode subsystems of a medical device system are arranged about a patient's heart 710. The medical device includes a first electrode subsystem, comprising a can electrode 702, and a second electrode subsystem 704 that includes at least two electrodes or at least one multi-element electrode. The second electrode subsystem 704 may include a number of electrodes used for sensing and/or electrical stimulation.

In various configurations, the second electrode subsystem 704 may include a combination of electrodes. The combination of electrodes of the second electrode subsystem 704 may include coil electrodes, tip electrodes, ring electrodes, multi-element coils, spiral coils, spiral coils mounted on non-conductive backing, screen patch electrodes, and other electrode configurations as will be described below. A suitable non-conductive backing material is silicone rubber, for example.

The can electrode 702 is positioned on the housing 701 that encloses the medical device electronics. The medical device shown in FIG. 7 incorporates one or more sensors configured to sense respiration. A sensing element, e.g., electrode, used for impedance sensing may be disposed on housing 701, such that element 702 may be representative of such electrode(s) alone or in combination with a can electrode. Sensing elements used for impedance sensing may be disposed on another component of the medical device, such as on lead 706, a lead separate from lead 706, or on the subsystem element 704, which may be representative of such sensing element(s) alone or in combination with a cardiac electrode. In addition to the electrodes previously described, a medical device of the present invention may include sensors configured to sense blood (internal filling) pressure, flow, and/or temperature, sense acceleration and/or body acoustics, and/or sense other physiological parameters of interest.

A medical device of the present invention may be implemented to communicate with a patient management server or network via an appropriate communications interface or an external programmer. A medical device of the present invention may be used within the structure of an advanced patient management (APM) system. The APM system allows physicians to remotely and automatically monitor cardiac and respiratory functions, as well as other patient conditions.

In one example, a medical device implemented as a cardiac pacemaker, defibrillator, or resynchronization device may be equipped with various telecommunications and information technologies that enable real-time data collection, diagnosis, and treatment of the patient. Various medical device embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

The components, functionality, and structural configurations depicted herein are intended to provide an understanding of various features and combination of features that may be incorporated in a medical device. It is understood that a wide variety of medical devices and other implantable cardiac monitoring and/or stimulation device configurations are contemplated, ranging from relatively sophisticated to relatively simple designs. As such, particular medical device or cardiac monitoring and/or stimulation device configurations may include particular features as described herein, while other such device configurations may exclude particular features described herein.

Figure 8:
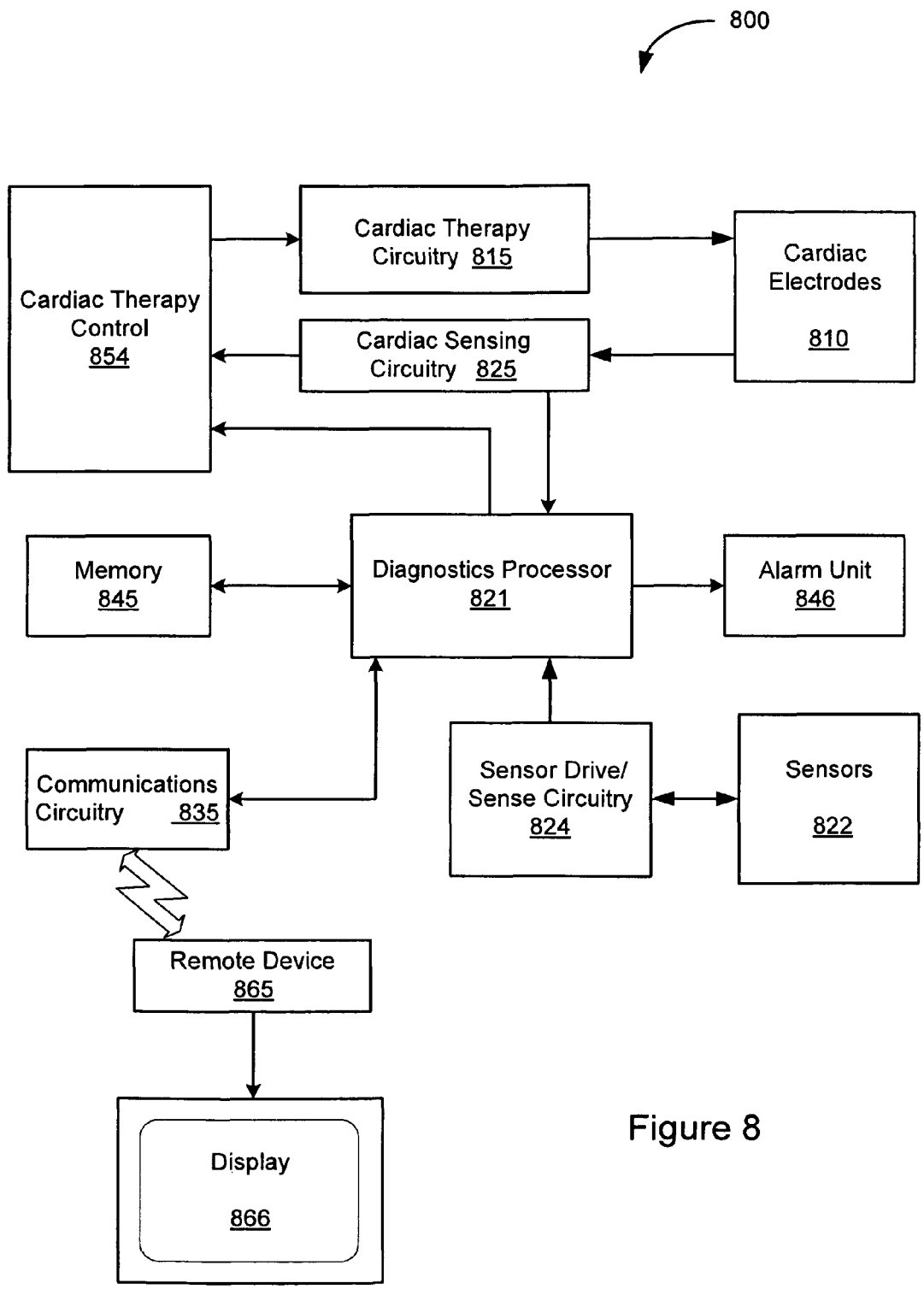
FIG. 8 is a block diagram showing a variety of illustrative operations that may be performed involving evaluation of heart failure symptoms in accordance with embodiments of the invention.

FIG. 8 illustrates a block diagram of a system 800 suitable for evaluation of CHF symptoms in accordance with embodiments of the invention. As previously discussed, in some embodiments, sensors and other circuitry components used for CHF symptom evaluation based on cumulative sum analysis are implemented in conjunction with an implantable cardiac rhythm device. The cardiac rhythm device includes cardiac electrodes 810 that are electrically coupled to the patient's heart. Electrical signals from the patient's heart are sensed via the cardiac electrodes 810 and cardiac sensing circuitry 825. The cardiac therapy control circuitry 854 may detect arrhythmic conditions, such as bradyarrythmia or tachyarrhythmia, based on the sensed cardiac electrical signals. Cardiac therapy control circuitry 854 controls cardiac therapy circuitry 815 which generates electrical stimulation pulses delivered to the heart through the cardiac electrodes 810 to treat various heart rhythm irregularities. For example, the cardiac therapy circuitry 815 may generate a series of low energy electrical pacing pulses timed to assist the heart in maintaining a hemodynamically appropriate rhythm and synchronization. The cardiac therapy circuitry 815 may generate high energy shocks delivered to the heart if the cardiac control circuitry 854 detects tachycardia or fibrillation, arrhythmic conditions producing a heart rate that is too fast and possibly lethal.

The system 800 may include one or more sensors 822 for sensing physiological parameters and acquiring data associated with CHF symptoms. The sensors 822 are coupled to a diagnostics processor 821 which is configured to perform cumulative sum analysis of the sensor signals. The sensors 822 may be implantable or patient-external. In some configurations, the diagnostics processor 821 may be disposed within the housing of an implantable device, such as a cardiac pacemaker. In this configuration, external sensors 822 are communicatively coupled with the diagnostics processor 821 of the implanted device via a wireless communications link. Similarly, if the diagnostics processor 821 is positioned external to the patient, implanted sensors 822 are wirelessly coupled to a patient-external device.

Sensor drive/sense circuitry 824 provides the necessary drive signals to activate the sensors 822 and also conditions the sensor response signals. For example, the drive/sense circuitry 824 may be configured to perform sampling, filtering, analog to digital conversion, and/or other processing of the sensor data. In addition to sensed data, information may be input to the system 800 via a remote device 865. For example, patient weight information may be manually entered by the patient into the diagnostics processor 821 through the remote device 865.

In some implementations, the diagnostics processor 821 may pre-process the data to derive certain parameters from the sensed or manually entered data. For example, the diagnostics processor 821 may include circuitry for detecting disordered breathing episodes from a respiration signal generated by a sensed transthoracic impedance signal. The diagnostics processor 821 may derive an index representative of a severity of disordered breathing, such as an apnea/hypopnea index (AHI) which is a measure of the number of disordered breathing episodes per unit of time. A cumulative sum evaluation of the AHI may be performed to assess CHF progression. As another example, the diagnostics processor 821 may analyze a cardiac electrogram sensed via the cardiac electrodes 810 and cardiac sensing circuitry 825 to derive heart rate variability (HRV) or other parameters associated with cardiac function. The diagnostics processor 821 may perform a cumulative sum evaluation of HRV. As previously mentioned, a representative set of data acquired for CHF evaluation may include one or more of the following parameters: transthoracic impedance, respiratory rate, S3 or S4 gallop heart sounds, heart rate variability, weight, activity, and apnea hypopnea index, among other parameters indicative of CHF symptoms.

The trend developed by the diagnostics processor 821 may be stored in memory 845 and may be downloaded to the remote device 865 periodically or on request. The diagnostics processor 821 is configured to evaluate the sensor data trend using cumulative sum techniques, such as those described in the exemplary embodiments provided herein. The diagnostics processor 821 compares the cumulative sum to a threshold or V-mask to determine if a persistent shift in sensor data indicates worsening of the CHF symptoms being evaluated. A display unit 866 may be coupled to the remote device 865 (in wireless communication with communications circuitry 835) to display data trends, alert messages, and/or other information associated with CHF including the progression or regression of CHF or various symptoms associated with CHF.

In one embodiment, if a persistent shift is detected, the diagnostics processor 821 controls an alarm unit 846 to generate an alert to the patient or physician. The alert may be an audible, visual and/or vibratory alert, and may be communicated to the patient or other person via an email, pager or telephone message. In another embodiment, if a persistent shift of the data is detected, the diagnostics processor 821 may generate a control signal received by the therapy unit 854. In the illustrated embodiment, the control signal initiates, terminates, or modifies an electrical stimulation therapy delivered to the patient.

A system according to the present invention may include one or more of the features, structures, methods, or combinations thereof described herein. For example, a cardiac monitor, cardiac stimulator, drug pump, or other type of implantable, partially implantable, or patient-external medical device may be implemented to include one or more of the advantageous features and/or processes described above. It is intended that such an implanted, partially implanted or patient external device need not include all of the features described herein, but may be implemented to include selected features that provide for useful structures and/or functionality. Such a device may be implemented to provide a variety of therapeutic or diagnostic functions.

The implementation described in connection with FIG. 8 presumes that diagnostics processor 821 performing the evaluation of sensor data for CHF is performed by an implantable device. In other configurations, these processes may be performed by a patient-external device, such as the remote device 865, or by two or more implantable or patient-external devices that are communicatively coupled. For example, in one configuration, an implantable device may perform one subset of the functions described above and a remote device, which may be a device programmer or advanced patient management system, may perform another subset of the functions.

Various modifications and additions can be made to the preferred embodiments discussed herein above without departing from the scope of the present invention. Accordingly, the scope of the present invention should not be limited by the particular embodiments described above, but should be defined only by the claims set forth below and equivalents thereof.

What is claimed is:

1. A method, comprising:
   acquiring sensor data associated with one or more symptoms of heart failure;
   calculating a cumulative sum from the sensor data;
   evaluating the cumulative sum to determine a change in the one or more heart failure symptoms by comparing the cumulative sum to one or both of a threshold and a V-mask, wherein the cumulative sum exceeding the threshold or the V-mask indicates change in the one or more heart failure symptoms; and
   generating an output in response to the cumulative sum exceeding one or both of the threshold and the V-mask, wherein generating the output comprises at least one of triggering an alert and changing delivery of a therapy, wherein at least one of evaluating, comparing, and generating is implemented at least in part by circuitry.

2. The method of claim 1, wherein acquiring the sensor data comprises:
   generating a transthoracic impedance signal; and
   extracting statistical features from the transthoracic impedance signal.

3. The method of claim 1, wherein acquiring the sensor data comprises:
   acquiring heart sounds data; and
   extracting statistical features from the heart sounds data.

4. The method of claim 1, wherein acquiring the sensor data comprises:
   acquiring patient activity data; and
   extracting statistical features from the patient activity data.

5. The method of claim 1, wherein acquiring the sensor data comprises:
   acquiring heart rate variability data; and
   extracting statistical features from the heart rate variability data.

6. The method of claim 1, wherein acquiring the sensor data comprises:
   acquiring apnea/hypopnea index data; and
   extracting statistical features from the apnea/hypopnea index data.

7. The method of claim 1, wherein the acquired sensor data comprises data associated with one or more cardiac parameters.

8. The method of claim 1, wherein acquiring the sensor data comprises acquiring data from a single sensor.

9. The method of claim 1, wherein:
   acquiring the sensor data comprises acquiring the sensor data from multiple sensors; and
   developing the cumulative sum comprises developing a multivariate cumulative sum.

10. The method of claim 1, acquiring the sensor data comprises acquiring the sensor data based on signals sensed within a moving time window.

11. The method of claim 1, wherein calculating the cumulative sum comprises:
    trending the sensor data in a moving window;
    determining a slope of the sensor data trended in the moving window; and
    calculating the cumulative sum of the slope.

12. The method of claim 1, wherein:
    evaluating the cumulative sum comprises detecting a shift in the cumulative sum; and
    generating the output comprises generating a status alert based on the shift.

13. The method of claim 1, wherein generating the output comprises controlling the therapy based on the evaluation of the cumulative sum.

14. The method of claim 1, wherein at least one of acquiring the sensor data, calculating the cumulative sum, evaluating the cumulative sum, and generating the output are performed at least in part by implantable circuitry.

15. A medical device, comprising:
    sensing circuitry configured to acquire sensor data associated with one or more symptoms of heart failure; and
    a diagnostics processor configured to calculate a cumulative sum of the sensor data, evaluate the cumulative sum to determine whether the cumulative sum exceeds one or both of a threshold and a V-mask indicating change in one or more heart failure symptoms, and generate an output in response to the cumulative sum exceeding one or both of the threshold and the V-mask.

16. The medical device of claim 15, wherein the sensing circuitry comprises a sensor configured to sense transthoracic impedance, the sensing circuitry configured to acquire the sensor data based on the transthoracic impedance signal.

17. The medical device of claim 15, wherein at least one of the sensing circuitry and the diagnostics processor comprises an implantable component.

18. The medical device of claim 15, wherein the diagnostics processor is configured to extract statistical features from the sensor data and to calculate the cumulative sum of the extracted statistical features.

19. The medical device of claim 15, wherein the diagnostics processor is configured to trend the sensor data, determine a slope of the trend, and calculate the cumulative sum of the slope.

20. The medical device of claim 15, wherein the medical device further comprises an alarm unit coupled to the diagnostics processor, the diagnostics processor is configured to evaluate the cumulative sum by detecting a shift in the cumulative sum, and the alarm unit is configured issue an alert when the shift exceeds one or both of the threshold and the V-mask.

21. The medical device of claim 15, wherein the medical device further comprises a therapy control unit coupled to the diagnostics processor, the therapy control unit used to control a therapy based on the evaluation of the cumulative sum indicating one or more heart failure symptoms.

22. The medical device of claim 21, wherein the therapy comprises a cardiac pacing therapy.

23. A medical system, comprising:
   means for acquiring sensor data associated with one or more symptoms of heart failure;
   means for calculating a cumulative sum of the sensor data;
   means for evaluating the cumulative sum to determine a change in the cumulative sum relative to one or both of a threshold and a V-mask, wherein the cumulative sum exceeding the threshold or V-mask indicates a change in one or more heart failure symptoms; and
   means for generating an output in response to the cumulative sum exceeding one or both of the threshold and the V-mask.

24. The system of claim 23, further comprising:
   means for generating a respiration signal; and
   means for extracting statistical features from the respiration signal.

25. The system of claim 23, further comprising:
   means for detecting a shift in the cumulative sum; and
   means for generating a status alert based on the generated output.

26. The system of claim 23, further comprising means for controlling a therapy based on the generated output.

27. The system of claim 26, wherein the therapy is biventricular pacing.

* * * * *

UNITED STATES PATENT AND TRADEMARK OFFICE
CERTIFICATE OF CORRECTION

PATENT NO. : 7,761,158 B2
APPLICATION NO. : 11/312277
DATED : July 20, 2010
INVENTOR(S) : Brockway et al.

It is certified that error appears in the above-identified patent and that said Letters Patent is hereby corrected as shown below:

In the Specification:

Col. 10, line 4: "bradyarrythmia" should read --bradyarrhythmia--.

Signed and Sealed this

Ninth Day of November, 2010

David J. Kappos
*Director of the United States Patent and Trademark Office*